United States Patent [19]
Herzberg

[11] Patent Number: 5,782,785
[45] Date of Patent: Jul. 21, 1998

[54] KNEE BRACE

[75] Inventor: Thorsten Herzberg, Hamburg, Germany

[73] Assignee: Beiersdorf Aktiengesellschaft, Hamburg, Germany

[21] Appl. No.: 728,402

[22] Filed: Oct. 9, 1996

Related U.S. Application Data

[63] Continuation of Ser. No. 413,707, Mar. 28, 1995, abandoned.

[30] Foreign Application Priority Data

Apr. 1, 1994 [DE] Germany .................... 44 11 469.9

[51] Int. Cl.$^6$ .................................................. A61F 5/00
[52] U.S. Cl. .................................... 602/26; 602/16
[58] Field of Search ........................... 602/516, 16, 20, 602/21, 23, 26; 128/845, 846, 869, 878, 882

[56] References Cited

U.S. PATENT DOCUMENTS

| | | |
|---|---|---|
| 3,831,467 | 8/1974 | Moore . |
| 4,624,246 | 11/1986 | Ajemian .................... 602/26 |
| 5,119,805 | 6/1992 | Cadoret .................... 602/26 X |
| 5,121,742 | 6/1992 | Engen .................... 602/26 X |
| 5,277,698 | 1/1994 | Taylor .................... 602/26 |

FOREIGN PATENT DOCUMENTS 3123148   12/1989   Germany .
4229044   3/1993    Germany .

Primary Examiner—Linda C. Dvorak
Attorney, Agent, or Firm—Friedrich Kueffner

[57] ABSTRACT

The knee brace (100) with a casing to be applied to the leg and held together on the front side of the leg with the aid of fastening straps of a padded frame is comprised of a frame (10), of a half shell-shaped frame portion (11) which can be applied dorsally to the thigh and a half shell-shaped frame portion (111) which can be dorsally applied to the lower leg, wherein both frame portions (11;111) are rigidly or articulatedly interconnected and each frame portion (11; 111) is formed by a U-shaped bar section (12;112) with an approximately semicircularly proceeding web (13;113) for application to the rear of the thigh or of the lower leg, to which a plurality of one-armed fixation rods (16, 16a, 16b, 16', 16a', 16b'; 116, 116a, 116b; 116', 116a', 116b') which are attached with one end, which proceed in the longitudinal direction of the knee brace (100), which are deformable, springable and which possess a high degree of inherent rigidity and which are adapted to the anatomic configuration of the leg, are secured, while two frame portions (11;111) are interconnected in such a way that their two U-shaped bar sections (12;112) face each other, the knee brace (100), within the region of its two terminal areas, is provided with one fastening strap (20;120) each and, above and below the knee, is provided with one further fastening strap (30;130) each (FIG. 1).

16 Claims, 11 Drawing Sheets

KNEE BRACE

This is a continuation, of application Ser. No. 08/413,707 filed Mar. 28, 1995, now abandoned.

The present invention relates to a knee brace with a casing to be applied to the leg held together on the front side of the leg with the aid of fastener straps of a padded frame portion.

BACKGROUND OF THE INVENTION

Sugical interventions on the knee call for a postoperative immobilization which, classically, is established by means of a functional plaster cast. Typically, plastic plasters or splints are bent with the aid of elastic bands. Where mobile patients are involved, these bands are frequently replaced by VELCRO type hook and loop strip fasteners which are fitted direct to shell-shaped splints. In order to enhance the wear comfort, these shells are often padded.

From DE-A-31 23 148, a knee brace possessing a flexible shell or casing is known, whose lateral rims, after the application of the shell to the leg, are held together on the front side of the leg and which possess one recess each for the kneecap, along the lateral rims, adjustable fastening elements are provided in which the shell, within those regions which, subsequent to the application of the shell to the leg, come to lie on the lateral areas and on the back of the leg. Reinforcement rods are also provided. The shell of this knee brace is composed of several anatomically true blanks, in which case the blanks and the reinforcement rods possess a configuration and curvature that is intended to fixate the knee joint in a flexed position of approximately 20°.

Also the knee brace according to the DE-A-42 29 044 is comprised of a flexible shell or casing which is provided with fastening elements on its lateral rims which, following the application to the leg, hold the shell together in the form of a closed tube. The longitudinal axis of the portion enclosing the lower leg assumes an angular position to the longitudinal axis of the thigh. In this knee brace, the blank forming the shell is of one-piece construction and can be unrolled in one plane. In the unrolled state, a recess is provided extending substantially parallel to the longitudinal axis of the leg which, along the direction of the leg, possesses larger dimensions than transversally thereto. On at least one of its ends, the recess does not reach the edge of the blank. When the knee brace is completed, the two longitudinally directed lateral edges of the recess are interconnected.

In the two first-mentioned cases, the knee braces are comprised of a flexible shell or casing. If this shell is composed of several blanks, then a high degree of accuracy is always required when the sewing work is done. An inaccurate side-by-side disposition and joining together of the individual blanks may lead to an incorrect shape and, with this, to a poor fit of the brace. Both the known knee braces are constructed in such a way that they fixate the knee joint in a predetermined flexed position of approximately 20°. In such a case a loosening or slackening of the knee brace which may occur in the course of the treatment is correctable. In order to retain this predetermined position, the shells of the knee braces are composed of several anatomically true blanks. The in which case the blanks and the stiffening rods possess a configuration and curvature intended for the fixation of the knee joint in a flexed position of approximately 20°. Due to the predetermined shells forming the knee braces, problems related to a good fit and proper fitting often do arise. Finally, these known knee braces have to be made to measure. Moreover, even with an immobilized knee, the patient is unable to perform any stretching exercises with the known knee braces. Since, in the applied state, the shells of these known knee braces ensheath the leg on all sides, a heat build-up cannot be avoided.

From the U.S. Pat. No. 3,831,467, an orthopedic appliance for the knee is known which is comprised of an elastic fabric that is applied in a casing-like fashion within the region of the knee on thigh and lower leg and held in position on the leg by a great number of fastening bands. In the applied state, the leg is completely enclosed with only an aperture for the patella left open. In order to produce a stiffening of the appliance by means of which a flexing of the knee is meant to be prevented, stiffening rods are provided on the fabric. Three central stiffening rods opposite the patella, are provided. The stiffening rods disposed directly behind the hollow of the knee, are the most important ones. In addition, one stiffening rod each may be provided laterally on top of that. On account of the natural hollow space of the back of the knee, the stiffening rods there do not rest on the leg, which may give rise to a sliding to and fro of the orthosis on the leg, even when the fastening bands are tightened. For this reason, a soft padding is affixed to the internal surface area of the knee orthosis at this point. This padding merely fill the hollow of the knee, but fails to keep the knee in the flexed position of from 10° to 20°. This is necessary for a successful treatment since the padding possesses a relatively flat configuration and it is only intended to contribute to reduce a slipping out of position of the applied orthosis.

It is the object of the present invention to provide a knee brace which is employable postoperatively or, if injuries to the leg are involved, for immobilizing the knee joint in an extended position, expediently in a functional flexed position, while including a mobility of the leg within a predetermined angular range. A further object is the possibility of being able to vary the same in adaptation to the course of the convalescence, which makes an adaptation to the anatomy of the leg and an accurate positioning of the knee joint possible. Accordingly, the knee brace has to possess a symmetric construction so as to make it possible for the same to be used for both the left and the right leg.

SUMMARY OF THE INVENTION

Accordingly, the casing constituting the knee brace possesses a preferably metallic frame of a short, half shell-like upper frame portion that can be dorsally applied to the thigh and a lower, longer, half shell-shaped frame portion which can likewise be dorsally applied to the lower leg. Each frame portion is formed of a U-shaped bar section with an approximately semicircularly proceeding web for resting on the thigh or lower leg. Laterally and adjacent to the two bar section legs, a plurality of one-armed, dorsal fixation rods are attached with one end and proceeding upwardly and downwardly in the longitudinal direction of the knee brace, the rods are springable and possess a high degree of inherent rigidity and are approximately adapted to the anatomic configuration of the thigh and lower leg so that a flexible, yet stable casing possessing subsequent forming possiblities is obtained. This makes it possible to effortlessly adapt the knee brace to the anatomy of the leg. Furthermore, the knee brace is, within the area of its terminal regions, provided with one fastening strap and one further fastening strap each which, when the knee brace is applied, proceeds above and below the knee.

According to further features of the invention, the two frame portions of the knee brace frame are articulatedly interconnected with the aid of hinges. The hinges are constructed in such a way that the two frame portions of the knee brace frame, when the knee brace is applied, can be locked in a predetermined angular position or can be adjusted to an angular range with an angular position for a flexion or an extension of the leg. This permits a defined movement of the leg with the angular and/or motional range of the leg being variable and adaptable to the progress of the recovery. Consequently, depending on the continuing recovery of the leg, the possibility for a corresponding movement and flexion of the leg within the predetermined angular range does exist. The angular range is adjusted and varied in adaptation to the respective state of the leg so that a defined movement of the leg is achieved.

For the enhancement of the wearer's comfort, the frame portions of the knee brace frame are padded.

Due to the fastening straps for mounting the knee brace on the leg being positioned on the knee brace frame at specific points, viz. within the area of the knee brace ends and closely above and below the knee, an accurate positioning of the knee joint is possible. What is essential in this case is that the hinge axes of the hinges interconnecting the two frame portions are congruent, i.e. in full coincidence, with each other. With the aid of this knee brace, the leg is firmly positioned and held fast well within the region of the knee. Despite of the certain flexibility possesses by the two half shells of the knee brace, a high degree of stability does exist. The employment of dorsal fixation rods makes an effortless adaptation of the knee brace to the anatomy of the leg possible. The flexibility of these fixation rods also makes a later reshaping and fitting of the knee brace possible, which is feasible owing to the fixation rods being dorsally attached above and below the knee on the knee brace frame.

To this is added the fact that the knee brace manages with a small number of fastening and retaining straps. By preference, the attachment of the knee brace is effected at four points of the leg, in which case an immovable fit of the applied knee brace is achieved in particular by the knee brace being retained on the leg with the aid of two fastening straps which proceed above and below the knee.

The padding of the knee brace frame is provided with the aid of two padding blanks which can be slid onto the frame portions. The rear is provided with a plurality of pockets with insertion apertures corresponding to the number of fixation rods of the frame portions, into which the fixation rods of the two frame portions of the knee brace frame are inserted. The top padding blank is slid onto the fixation rods of the upper frame portion and the bottom padding blank is slid from below onto the fixation rods of the lower frame portion. The attachment and the mounting of the padding blanks is effected with the aid of suitable connecting means, such as e.g. press studs, VELCRO type hook and hook strip fastener connections. It is possible, however, for differently constructed fastening means to be employed.

Added to this is the circumstance that the immovable mounting of the knee brace applied to the leg is achieved in particular by the disposition of the four fastening straps, of which in each case the upper and the lower fastening strap is provided on the paddings. The fastening straps proceeding within the knee region, i.e. above and below the knee, are attached to the two frame portions of the knee brace frame. In this manner the knee brace frame is retained on the leg direct and not exclusively by means of the padding blanks.

For relieving the patella of pressure, a cushion or pressure-reducing pad is disposed on the fastening strap proceeding above the knee which, by virtue of its configuration, makes an adaptation to the patella possible. The patella is relieved in this fashion when the knee brace is applied. It is also possible for a cushion or pressure-reducing pad to be provided on the fastening strap which proceeds below the knee.

The knee brace is thus comprised of a basic frame structure with two half shell-like and stable, padded frame portions bearing fastening straps within their terminal regions.

By means of this construction, a flexible, yet stable, half shell is obtained, into which a leg can be placed. After the attachment of the fastening means, a casing enclosing the leg is provided. In order to keep the knee in the flexed position or in order to provide a defined motional range for the leg, the two frame portions of the knee brace frame with their paddings are brought into a predetermined angular position or are set to a predetermined angular range. Thereafter, the hinges which interconnect the two frame portions are set to the desired motional range of the leg.

Still further advantages are achieved with the knee brace constructed according to the invention as detailed below.

A very open construction without any heat build-up.

A good stabilization of the knee.

Simple handling due to preferably only four fastening means.

Good fit, low weight and adaptability to the anatomy of the respective leg to which the knee brace is to be applied.

The knee brace can be opened without problem on the reclining patient; the angular position or the motional play of the two frame portions of the knee brace frame can be effortlessly varied at any time in order to be able to adapt the flexing range of the leg to the respective state of recovery so that a joint guidance and leg movement in flexion and extension is possible.

Due to the preferably tubular fixation rods on both frame portions of the knee brace frame the knee brace adapts better to the leg.

The fixation rods serve to stabilize the leg and can simply be bent aside so as to accurately fit the knee brace, if this were to be necessary.

The surgical wounds are not covered by a bandage.

The knee brace offers a high degree of therapeutic safety. The knee is immobilizable and can be stabilized in a defined manner. A continuous, constant stabilization effect is achieved. The knee is immobilized in a defined, slightly flexed position, which relaxes the anterior cruciate ligament. The knee brace fits well to the leg and is retained in a stable fashion. A good soft tissue support is obtained both on the thigh as well as on the lower leg. The knee brace can be adapted to different thigh and lower leg widths.

Moreover, with the knee brace, a high degree of wearer comfort is obtained because the knee brace does not chafe, does not constrict, wears only slightly, is very light by virtue of its low weight; it is kind to the skin, impervious to air and vapor and possesses no unpleasant heat effect. The knee brace is simple to apply. The healing process can be readily checked. A postoperative wound care is possible. By the use of suitable materials, the knee brace is resistant to soiling. By the employment of separate padding blanks which are affixed to the frame portions of the knee brace frame, the padding can be effortlessly removed, cleaned an disinfected.

Further developments of the invention are the subject matter of the subclaims.

BRIEF DESCRIPTION OF THE DRAWINGS

Embodiment examples of the invention are illustrated in the drawings. This

DETAILED DESCRIPTION OF THE PREFERRED EMBODIMENT

Figure 1:
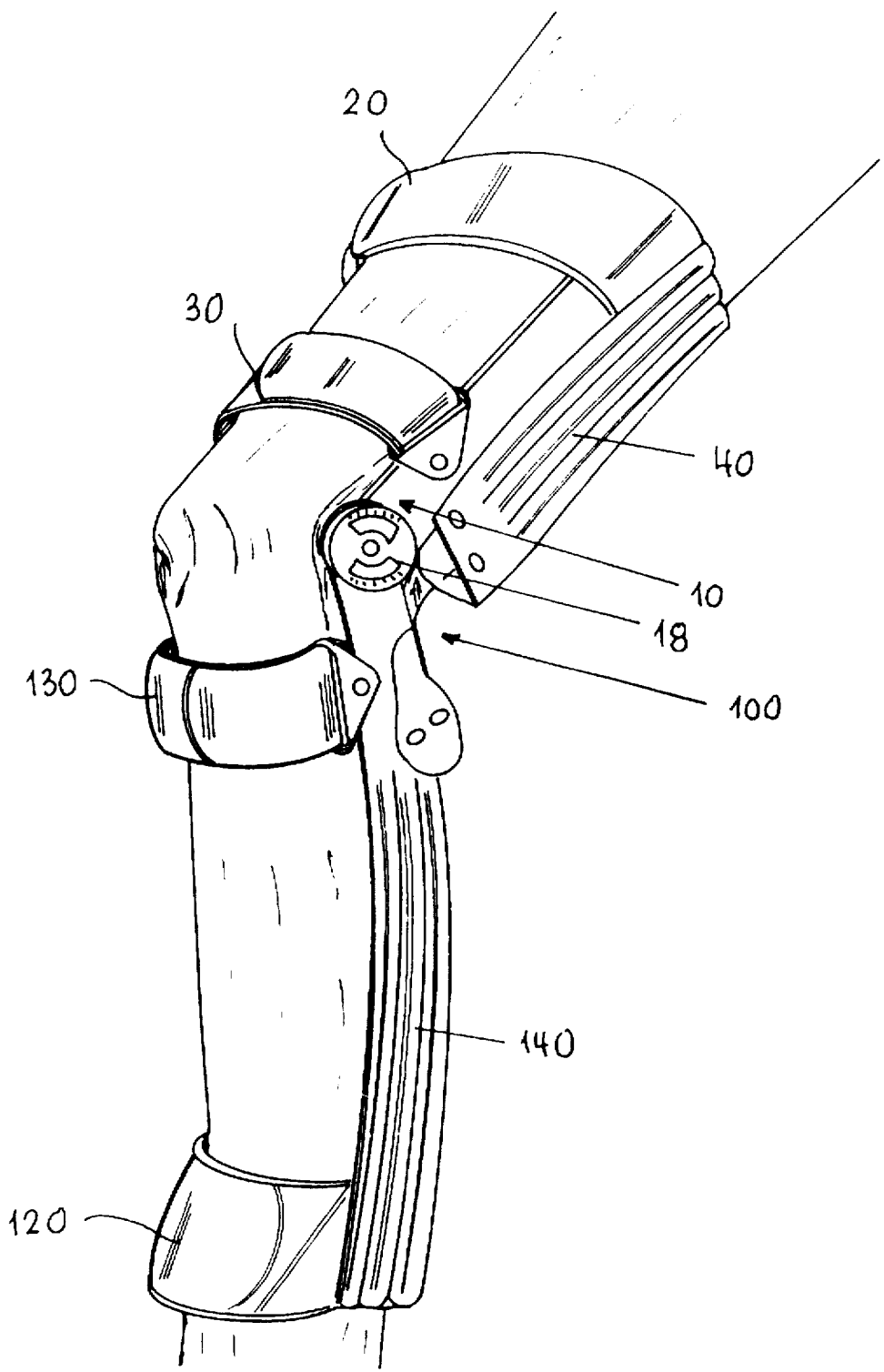
FIG. 1 shows in a diagrammatical view a knee brace applied to the thigh and lower leg of two half shell-shaped, padded orthosis portions.
Figure 2:
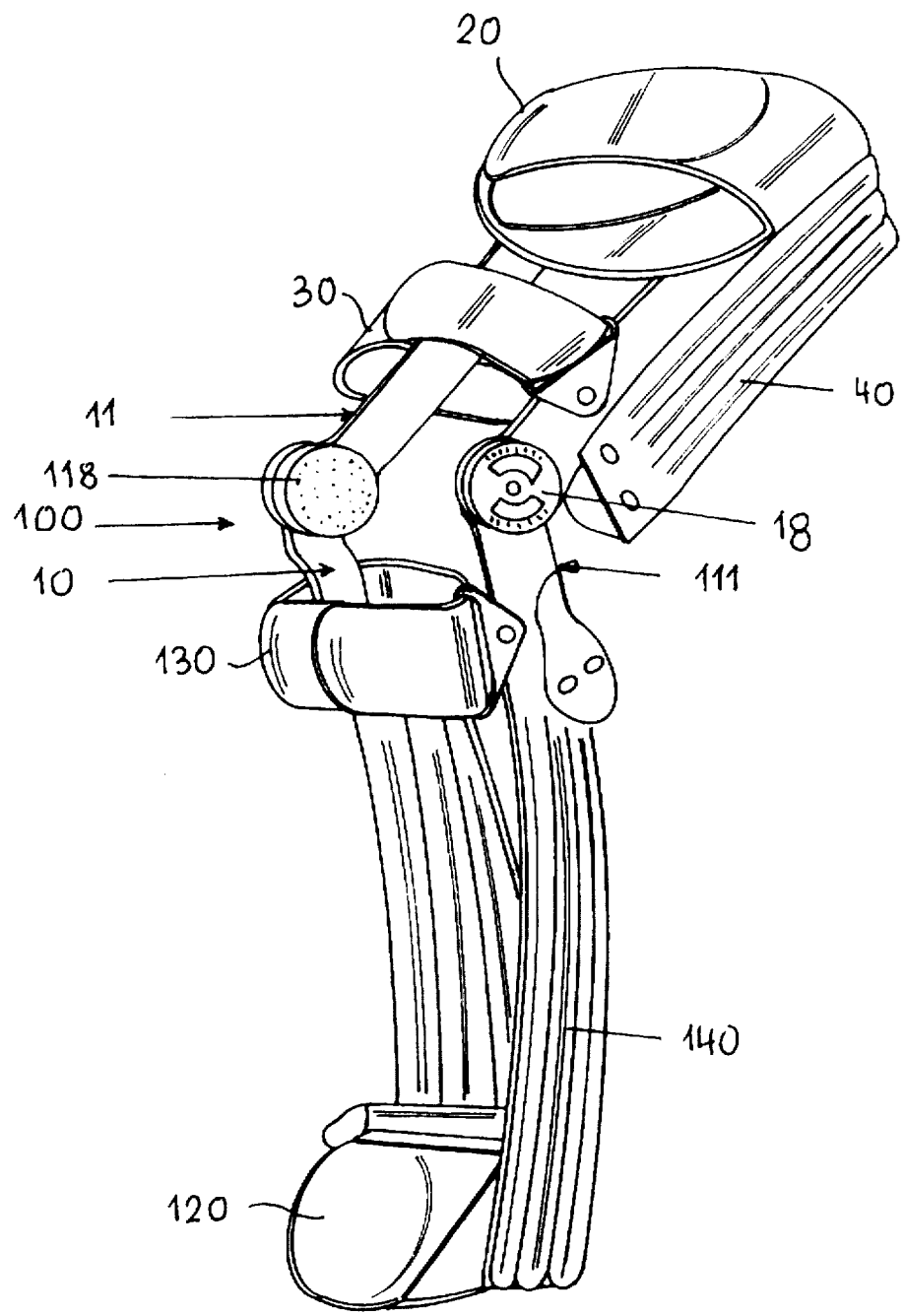
FIG. 2 shows in a diagrammatical view of the knee brace as per FIG. 1.
Figure 3:
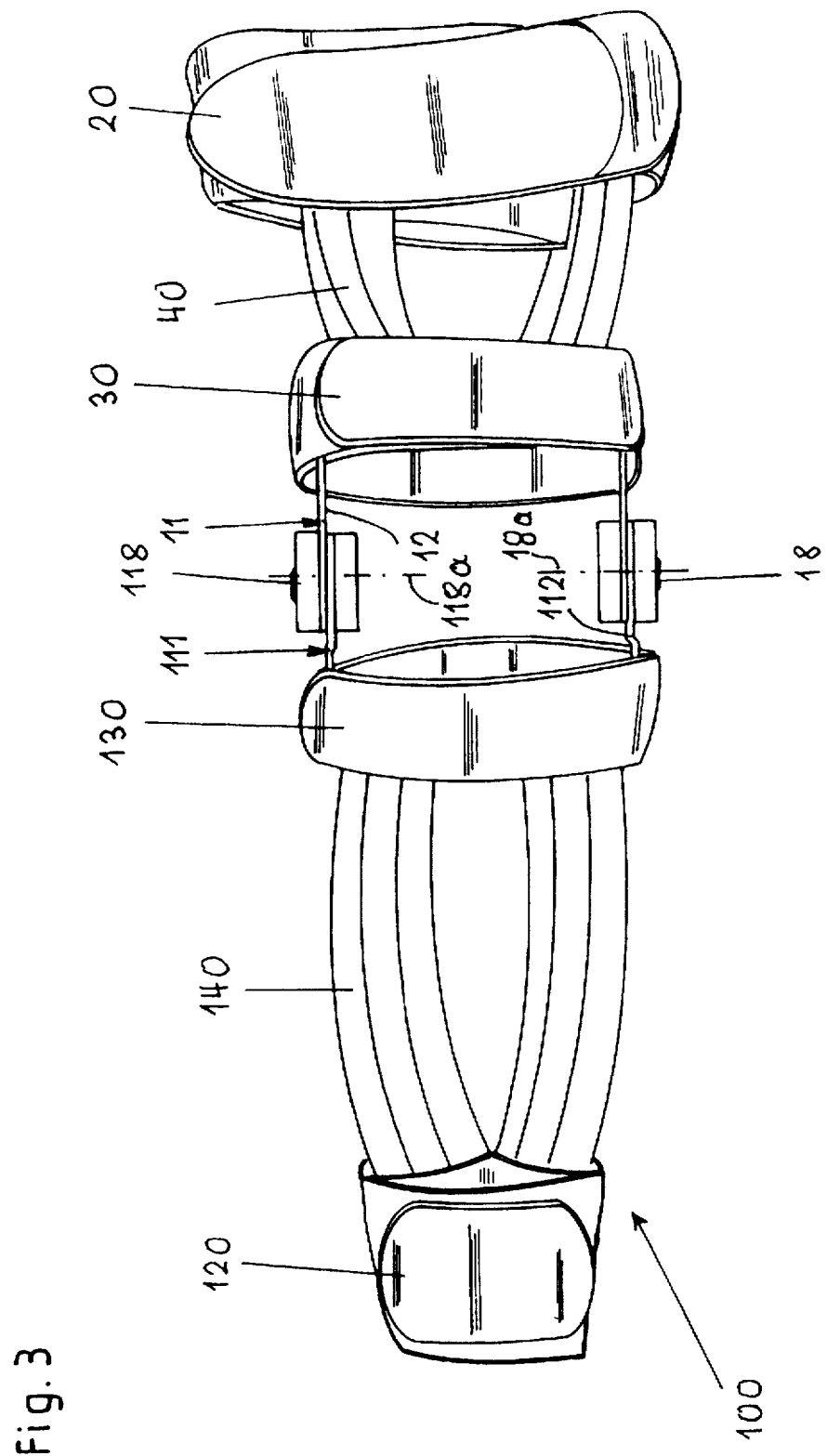
FIG. 3 shows the knee brace in a view from the top.
Figure 4:
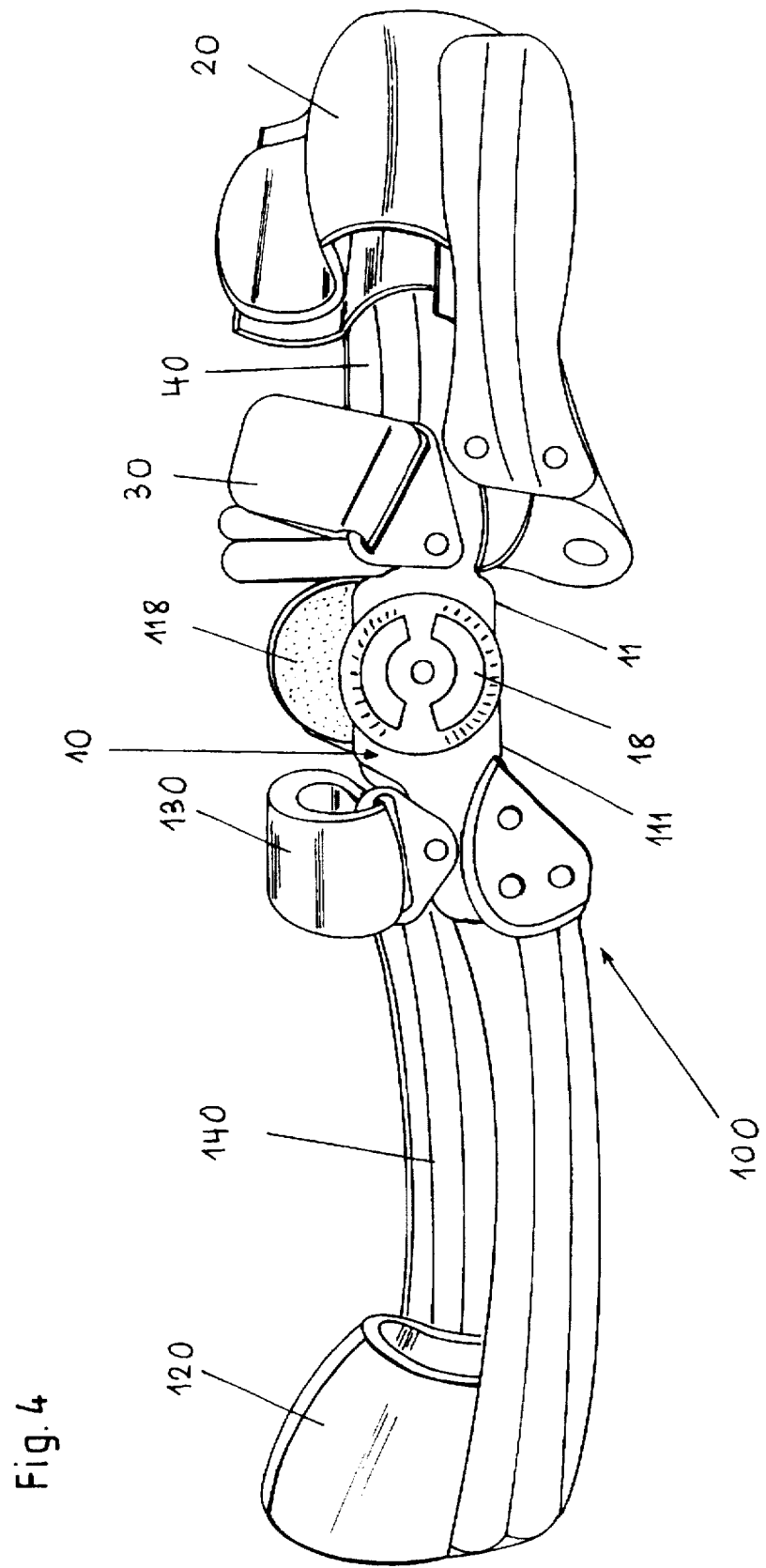
FIG. 4 shows in a side view of the knee brace with elongated frame portions.

According to FIGS. 1 through 4, the knee brace 100 is comprised of a casing to be applied to the leg of a patient and held together on the front side of the leg, which is formed of a padded frame 10 with fastening straps 20,120 and 30,130.

The knee brace 100 is comprised of a preferably metallic frame 10 of an upper, shorter, half shell-like frame portion 11 that is dorsally applicable to the thigh and a lower, longer, half shell-like frame portion 111 which is likewise dorsally applicable to the lower leg. Each frame portion 11,111 is formed of a U-shaped bar section 12 or 112 with an approximately semicircularly proceeding web 13 or 113 resting upon the thigh or lower leg. To the web 13 or 113 of each frame portion 11,111 of the knee brace frame 10, laterally and adjacent to the two bar section legs 14,15 or 114,115, a plurality of deformable, springable one-armed fixation are rods attached at one end. The rods proceed upwardly and downwardly in the longitudinal direction of the knee brace and possess a high degree of inherent rigidity and are adapted to the anatomic configuration of thigh and lower leg. The frame 10 may also be comprised of other materials, such as plastic or a carbon fiber material.

Figure 5:
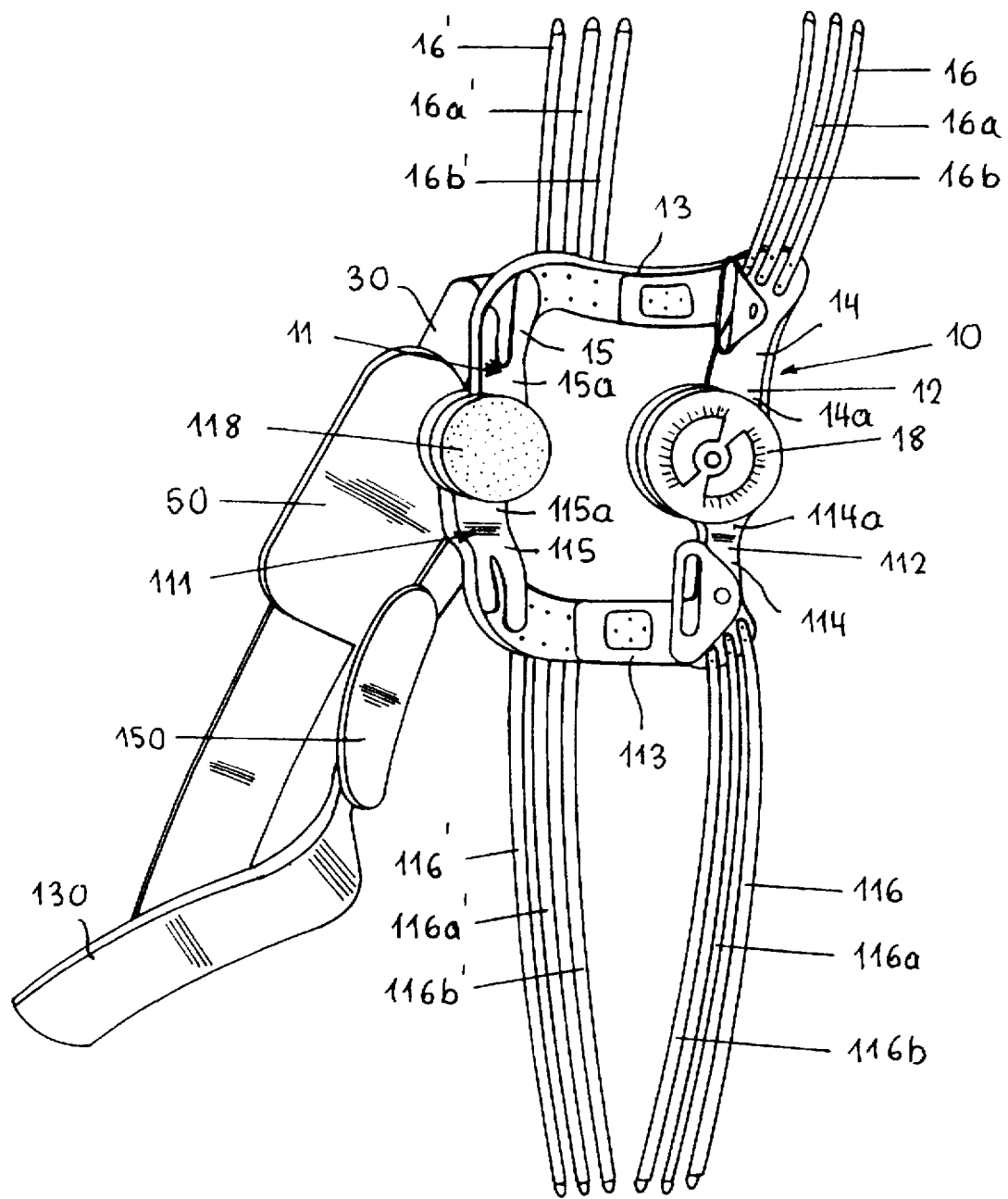
FIG. 5 shows a diagrammatical front view of the knee brace frame comprised of two hingedly interconnected frame portions.
Figure 6:
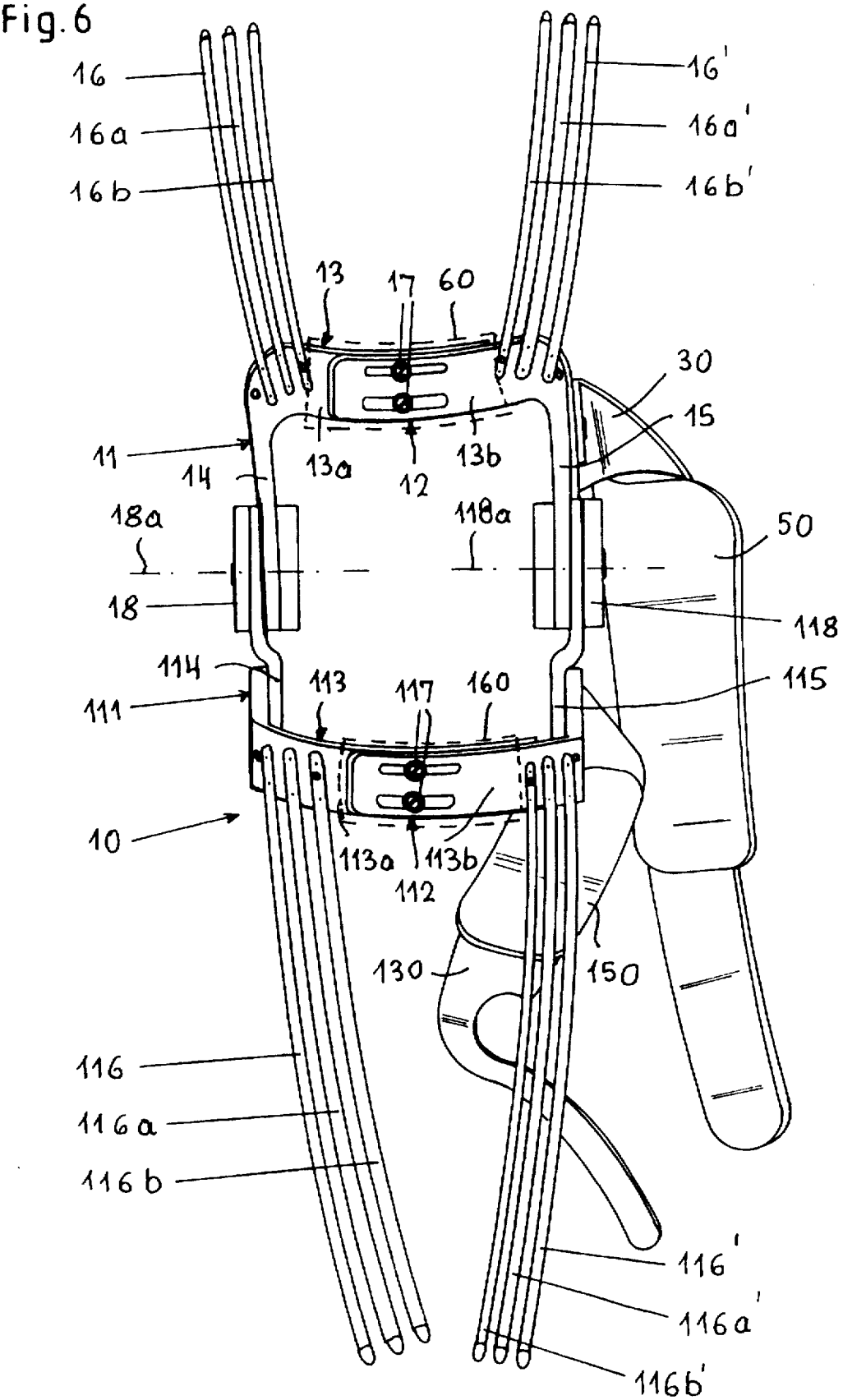
FIG. 6 shows a diagrammatical rear view of the knee brace frame.

In the embodiment depicted in the FIGS. 5 and 6, a frame 10 for the knee brace 100, is shown, the frame 10 having an upper frame portion 11, six fixation rods 16, 16a, 16b and 16', 16a', 16b'. Likewise six fixation rods 116, 116a, 116b and 116', 116a', 116b' are secured to the lower frame portion 111 likewise. In addition, three fixation rods 16, 16a, 16b and 16', 16a', 16b' and 116, 116a, 116b and 116', 116a', 116b' are combined in each case, while the thusly combined fixation rods of each frame portion 11,111 are disposed within the dorsal area of the thigh and the lower leg in such a way that half-shell-like configured frame portions 11,111 are formed which, when the knee brace 100 is applied, engage sectionwise over the thigh and lower leg.

The number the fixation rods of the upper frame portion 11 and of the lower frame portion 111 can be arbitrarily selected. The number of the fixation rods is not restricted to the number of fixation rods described and depicted in the foregoing. What is essential, though, is that the disposition of the fixation rods is such that half shelllike structures are produced which accommodate the thigh and the lower leg when the knee brace 100 is applied.

These frame portions 11,111 of the knee brace frame 10, together with the fastening straps 20,120 and 30,130, of a casing in the form of a flexible, yet stable half shell comprises two stable half shell portions and possesses a high degree of inherent rigidity and are adaptable to the contours of the leg.

The fixation rods on the frame portions 11,111 are of tubular construction and, by way of example, are comprised of aluminum or some other suitable material which, apart from a high degree of inherent rigidity, possesses a certain flexibility so as to be able to adapt to the fixation rods to the leg contours. These tubular fixation rods may also be comprised of a lightweight metal other than aluminum or of a fiber glass-reinforced plastic. A construction of the tubular fixation rods in the form of carbon fiber rods is also possible. What is essential, though, is that these tubular fixation rods do not possess a substantial weight.

It is also possible to employ tubular fixation rods of solid wall construction. The cross-section of the employed fixation rods may be circular, oval or may possess some other geometric cross-sectional configuration. The fixation rods employed in the knee brace 100 are, despite a high degree of inherent rigidity, deformable to a certain degree so as to be able to adapt the knee brace to the contours of the leg.

The two frame portions 11,111 can be rigidly interconnected so that a one-piece frame 10 for the knee brace is obtained. A thusly constructed knee brace 100 can only be employed for an extended position of the leg.

However, in order to be able to retain the leg in a predetermined flexed position or for a movement within a defined region of the knee brace 100, according to a further embodiment of the invention, the same is constructed in such a manner that the two frame portions 11,111 of the knee brace frame 10 are articulatedly interconnected by means of the free ends 14a,15a and 114a,115a of the legs 14,15 and 114,115 of the two U-shaped bar sections 12 and 112. In this way the two frame portions 11,111 can be set in each case at requisite angles in relation to each other. Both frame portions 11,111 are interconnected by means of hinges 18,118, which are operatively connected with locking means constructed in a manner known per se so that the in each case set angular position can be locked. It is consequently possible e.g. for locking means for the hinges 18,118 to be employed as described in the U.S. Pat. No. 4,982,732, in which a knee brace is shown having a casing to be applied to the leg held together on the front side of the leg. The casing is with the aid of fastening bands of two frame portions which are flexibly interconnected by means of hinges that are reciprocally lockable in the respective angular positions. However, by virtue of their constructional design, the frame not prevent a slipping out of position by the knee brace when worn.

The disposition of the hinges 18,118 interconnecting the two frame portions 11,111 is arranged in such a way relative to each other that their swivel axes 18a,118a lie congruently, i.e. are in full coincidence with each other and lie in one axial plane (FIGS. 5 and 6).

The fastening straps 20,30 and 120,130 are provided for mounting the knee brace 100 to the leg of a patient. Of these fastening straps, which will be dealt with in greater detail hereinafter, the fastening straps 20,120 are provided on the ends at both sides of the knee brace 100, while the two other fastening straps 30,130 located within the knee region are disposed in such a way that the fastening strap 30 is disposed a small distance above the knee. The fastening strap is disposed a small distance below the knee.

In order to be able to adapt two frame portions 11,111 of the knee brace frame 10 to differing configurations and sizes of the leg, the widths of the half shells formed by the frame portions 11,111 are variable. For this, the semicircularly proceeding web 13 or 113 of the two U-shaped bar sections 12 and 112 of each frame portion 11,111 is fabricated from two longitudinally variable rod sections 13a,13b and 113a, 113b. The two rod sections of each bar section 12 or 112 are lockable with the aid of a screwed connection, it being essential in this case that an automatic slackening of the locking means cannot take place.

The U-shaped bar sections 12,112, which form part of the two frame portions 11,111, are preferably comprised of a flat or strip section. The semicircularly constructed webs 13,113 and the bar section legs 14,15 and 114,114 are disposed so as to be vertical and offset by 90° relative to each other. In this way the webs 13,113 form a contact surface for the thigh or lower leg, whereas the lateral legs 14,15 and 114,115 of the two bar sections 12,112 proceed laterally of the leg (FIG. 6).

In order to achieve a good fit of the lower frame portion 111 of the knee brace frame 10 on the lower leg, the fixation rods 116,116a,116b and 116',116a',116b' of the lower frame portion 111 are preferably constructed so as to proceed straight with bends within the lower calf region.

Figure 7:
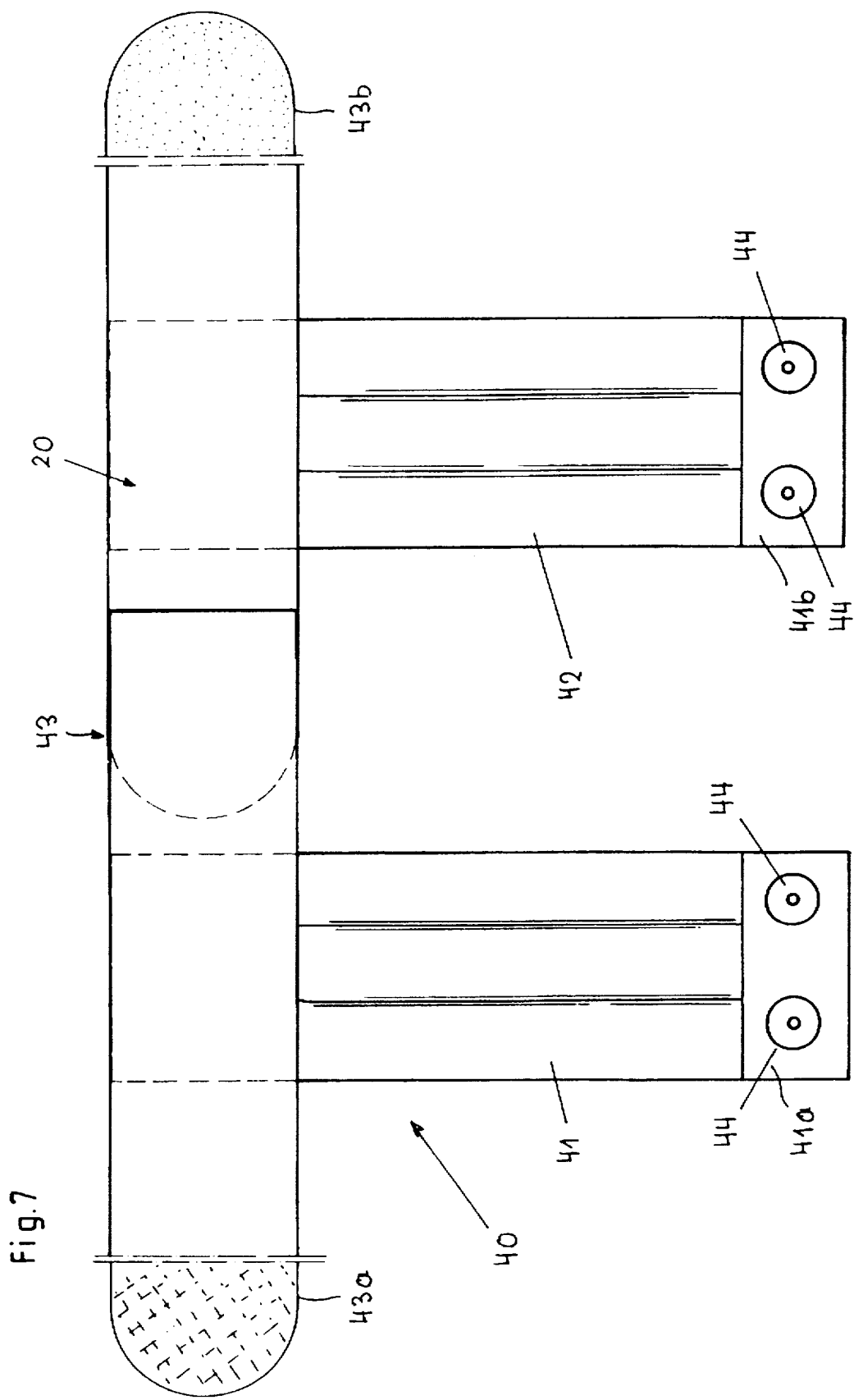
FIG. 7 shows a view onto the padded front side of the padding blank for the upper frame portion of the knee brace frame.
Figure 8:
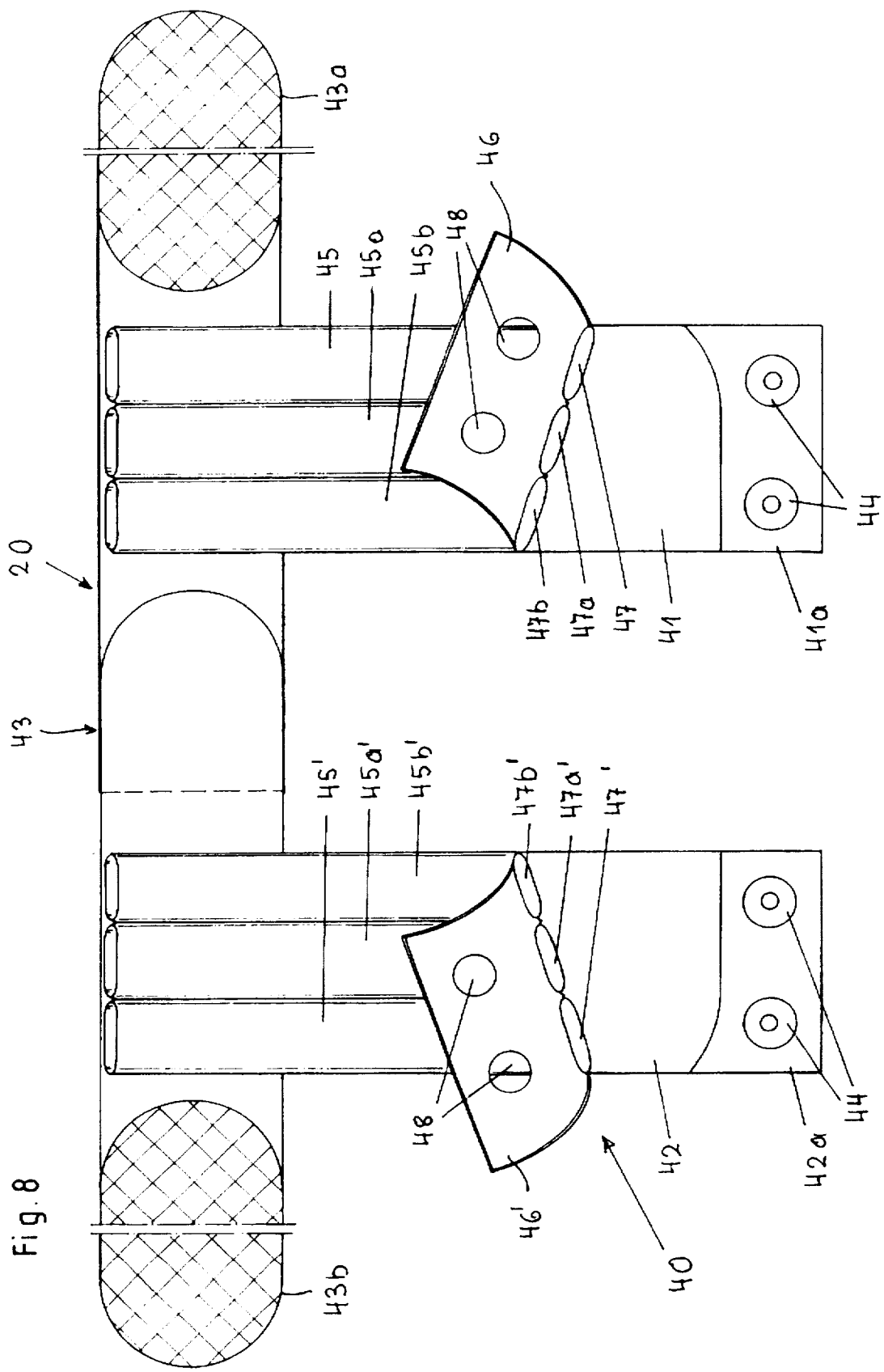
FIG. 8 shows in a rear view the upper frame portion of the knee brace frame as per FIG. 7.

The padding of the knee brace frame 10 is effected with the aid of two padding blanks 40,140 slidable onto the frame portions 11,111, of which each padding blank 40 or 140 is comprised of two strip-shaped side portions 41,42 and 141,142. The side portions 41,42 of the padding blank 40 resting on the thigh, are connected, by means of a top web 43, with laterally extended sections 43a,43b constructed in the form of fastening portions of a fastening strap 20. The free ends of the lateral sections 43a,43b are constructed as portions of a VELCRO type hook and loop strip fastener in order to produce the fastening effect when the knee brace is applied. The web 43 interconnecting the two side portions 41,42 of the padding blank 40 is preferably constructed in two parts, in which case both portions, within their overlapping area, are provided with parts of a VELCRO type hook and loop strip fastener so as to be able to detachably connect both portions. By means of this detachable connection, a longitudinal variability of the web 43 of the padding blank 40 is possible so as to, in adaptation to the width of the upper frame portion 11, be also able to adapt the padding blank 40 (FIGS. 7 and 8).

On the free ends of the two side portions 41,42 of the padding blank 40, tabs 41a,42a are formed with fastening means 44 which, by way of example, are constructed in the form of a press stud fastener.

The length of the side portions 41,42 of the padding blank 40 corresponds approximately to the length of the fixation rods 16, 16a, 16b and 16', 16a', 16b' disposed on the upper frame portion 11, which will be discussed in greater detail hereinafter.

Figure 9:
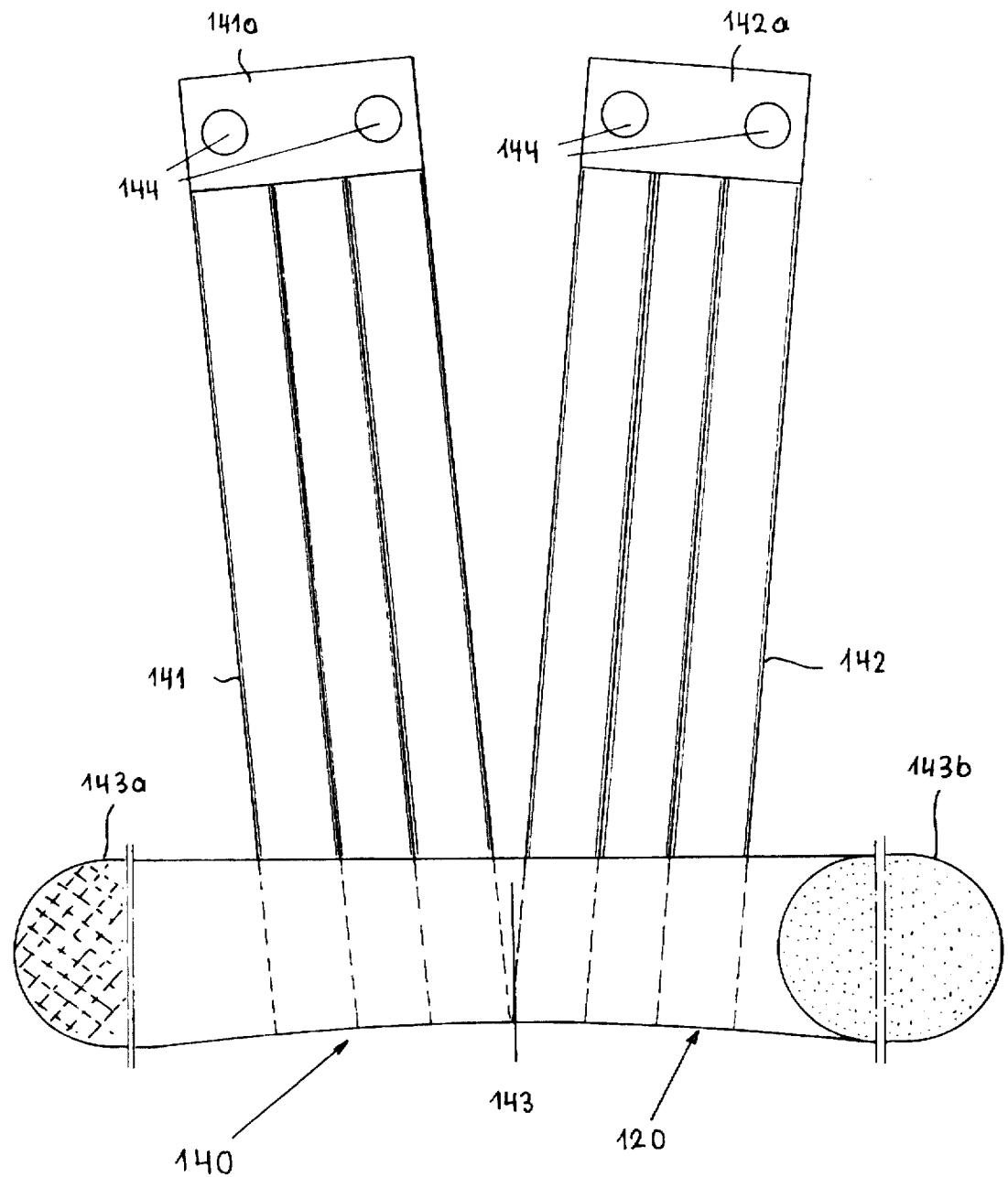
FIG. 9 shows a view of the padded front side of the padding blank for the lower frame portion of the knee brace frame.
Figure 10:
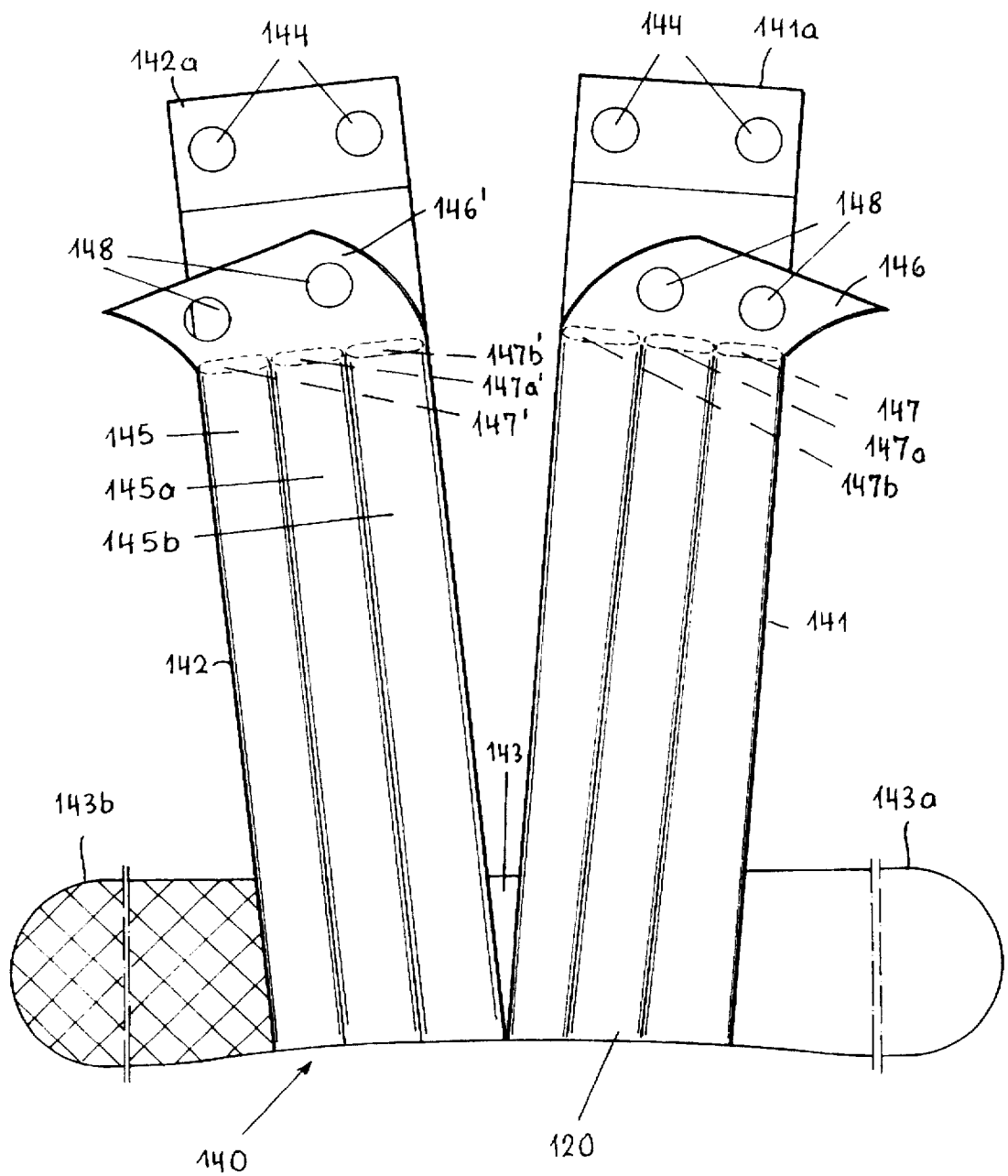
FIG. 10 shows in a rear view the lower frame portion of the knee brace frame as per FIG. 9.

The padding blank 140 slid onto the lower frame portion 111 of the knee brace frame 10 is constructed so as to be approximately correspond to the padding blank 40. Also in the padding blank 140, the two side portions 141,142 are on one side interconnected by means of a short web 143. In extension of the short web 143, lateral sections 143a,143b are formed onto the side portions 141,142 which, on their ends, are provided with the portions of a VELCRO type hook and loop strip fastener and, in the applied state of the knee brace 100, form the bottom fastening strap 120. The two side portions 141,142 of the padded blank 140 bear tabs 141a, 142a, to which fastening means 144, by way of example, press stud fasteners, are fitted (FIGS. 9 and 10).

Also in the case of the padding blank 140, an adaptation to the lower frame portion 111 of the knee brace frame 10 exists in so far as the two side portions 141,142 of the padding blank 140 are extended in a slightly V-shaped manner, which corresponds approximately to the anatomic course of the calf of the lower leg.

The surface areas facing the leg of the two padding blanks 40,140 are preferably comprised of a base fabric with an applied layer of a suitable padding material, in which case padding material of natural and of synthetic fibers can be used. It is also possible for springably resilient shaped plastic elements to be incorporated into the material of the padded blanks 40,140.

In order to be able to slide into the padding blanks 40, 140 the fixation rods on the frame portions 11,111 of the knee brace frame 10, the padding blanks are, on their back, provided with a plurality of pockets which terminate at one end in insertion apertures. The number of pockets for receiving the fixation rods 16, 16a, 16b and 16', 16a', 16b' or 116, 116a, 116b and 116', 116a', 116b' depends on the number of the fixation rods. In the embodiment described in the foregoing and depicted in the drawing, on the upper frame portion 11 and on the lower frame portion 111, six fixation rods each are provided, of which in each case three fixation rods are combined into a unit. According to this, the padding blanks 40,140 possess on their backs a number of pockets which corresponds to the number of these fixation rods.

In the padding blank 40, for the fixation rods of the upper frame portion 11 of the knee brace frame 10, the pockets 45, 45a, 45b and 45', 45a', 45b' with the insertion apertures 47, 47a, 47b and 47', 47a', 47b' are provided.

For receiving the fixation rods on the lower frame portion 111 of the knee brace frame 10, the padding blank 140 possesses on its rear the pockets 145, 145a, 145b and 145', 145a',145b' with the insertion apertures 147, 147a, 147band 147', 147a', 147b' (FIGS. 8 and 10). The length of the pockets on the backs of the padding blanks 40,140 corresponds to approximately the length of the fixation rods to be accommodated on the upper frame portion 11 and the lower frame portion 111 of the knee brace frame 10. Adjacent to the tabs 41a,42a of the side portions 41,42 of the padding blank 40 and the tabs 141a,141b on the side portions 146,146' are provided on the rear of the padding blanks 40,140. These blanks are provided with perforations 48, 148 so as to be able to introduce those parts of the press stud fastener which are provided on the tabs 41a,42a and 141a, 142a of the padding blanks 40,140, into the corresponding counterparts of the press stud fasteners. In this fashion the last-mentioned press stud parts are attached to the outsides of the semicircularly proceeding webs 13,113 of the U-shaped bar sections 12,112. With regard, to the fastening means it is also possible for other fastening means to be employed in lieu of press stud fasteners; what is essential here, though, is that the padding blanks 40,140 are detachably attached to the frame portions 11,111.

The formation of the pockets 45, 45a, 45b and 45', 45a', 47b' 145, 145a, 145b and 145', 145a', 145b' of the two padding blanks 40,140 is effected by means of a double-walled construction of the basic fabric blank for the padding blanks 40,140, in which case the formation of the pockets is produced by means of stitched connections.

The attachment of the two padding blanks 40,140 to the two frame portions 11,111 of the knee brace frame 10 is effected in that the tabs 41a,42a and 141a,142a of the two padding blanks 40,140 are laid around the semicircularly proceeding webs 13,113 and in that the two press stud fastening portions are brought into operative connection after the two padding blanks 40,140 have been slid over the fixation rods on the two frame portions 11, 111.

The upper and the lower fastening strap 20,120, respectively, of the knee brace 100 is secured to the padding blank 40 or to the padding blank 140. The two further fastening straps 30,130, which come to be located above and below the knee, are in comparison secured to the two frame portions 11,111 of the knee brace frame 10. In this case, too, it is possible for the fastening straps to be formed by tabs which possess VELCRO type hook and loop strip fastener-like connecting means. It is more advantageous, however, when the fastening straps 30,130 are constructed in the form of belt bands or webbing straps. For this, each fastening strap 30,130 is comprised of a band-like section which is passed through an eyelet affixed to the opposite side of the frame partions 11,111. The free end of each fastening strap, after having been passed through this ring or eyelet, is then attached to the adjacent fastening band section with the aid of a VELCRO type hook and loop strip fastener.

Figure 11:
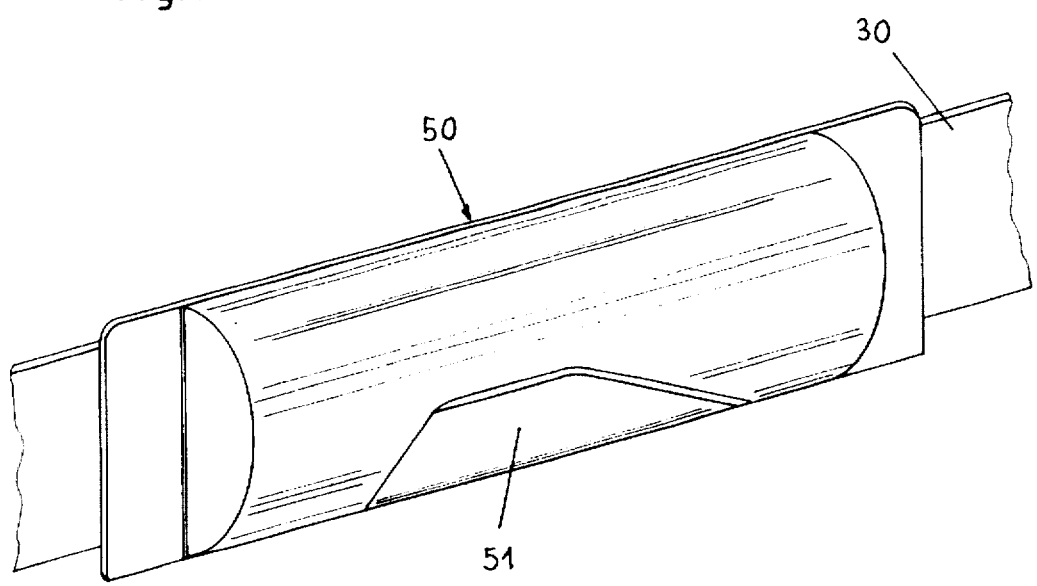
FIG. 11 shows in a diagrammatical front view a padding with formed recess for the patella slid onto the lower fastening strap of the upper frame portion of the knee brace frame.
Figure 12:
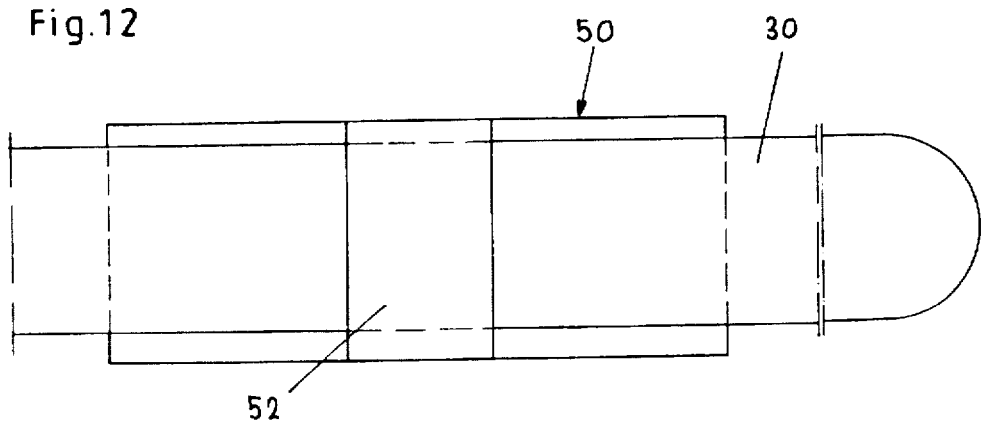
FIG. 12 shows in a rear view of the padding as per FIG. 11 displaceably attached to the lower fastening strap of the upper frame portion of the knee brace frame.

The fastening strap 30 provided within the lower area of the upper frame portion 11 of the knee brace frame 10 carries a pad or cushion 50 of a springably resilient material, such as e.g. a silicon rubber or some other suitable padding material, provided with a configuration adapted to the patella, which is indicated at 51 in FIG. 11. The pad 50 is retained on the fastening strap 30 in a rigid, detachable and/or displaceable manner. For the latter form construction, the pad 50 is provided on its rear with a fastening loop 52 (FIG. 12). Also on the fastening strap 130 proceeding below the knee, a pad or cushion 50 can be provided for supporting the knee.

The webs 13,113 of the frame portions 11,111 may be additionally provided with pads.

Further paddings may be provided on the semicircularly proceeding webs 13,113 of the bar sections 12,112 of the frame 10, as indicated in FIG. 6 with 60,160.

What is claimed is:

1. An orthopedic knee brace for use with a leg having an upper thigh portion, a lower calf portion and an intermediate knee region, said brace comprising:

an upper half shell frame portion applied dorsally to the upper thigh and formed by an U-shaped bar section, said U-shaped bar section having a semi-circular web and two ends;

a lower half shell frame portion applied dorsally to the calf portion of said leg and formed by an U-shaped bar section, said U-shaped bar section having a semi-circular web and two ends;

means for interconnecting said ends of said upper half shell frame portion with said ends of said lower half shell frame portion;

a first plurality of rigid one-armed fixation rods, having first and second ends, said first ends attached to said semi-circular web of said upper half shell frame portion and extending proximately to said upper half shell frame portion, said fixation rods having sufficient flexibility so as to adapt to the anatomic configuration of the user's thigh;

a second plurality of rigid one-armed fixation rods, having first and second ends, said first ends attached to said semi-circular web of said lower half shell frame portion and extending distally to said lower half shell frame portion, said fixation rods having sufficient flexibility so as to adapt to the anatomic configuration of the user's calf;

first fastening brace provided proximate said second ends of said first plurality of fixation rods for securing said fixation rods to said upper thigh;

second fastening brace provided proximate said second ends of said second plurality of fixation rods for securing said fixation rods to said calf portion;

third fastening brace provided proximate to said end of said upper half shell frame portion for securing said knee; and fourth fastening brace provided proximate to said end of said lower half shell frame portion for securing said knee.

2. The brace as set forth in claim 1, wherein said interconnecting means is provided with an adjustable hinge for adjusting the upper and lower frame portions at a predetermined angular position wherein said upper and lower half shell portion are articularly interconnected.

3. The brace as set forth in claim 1, wherein said semi-circular web of each of said upper and lower frame portions further comprise two longitudinally variable rod sections for adjusting the length of each of said semi-circular webs.

4. The brace as set forth in claim 1, wherein said interconnecting means is provided with first and second hinges rotating about an axis of rotation, said first and second hinges interconnecting said upper and lower frame portion.

5. The brace as set forth in claim 1, wherein said U-shaped upper and lower frame portions are provided with a flat band section and wherein said free ends are substantially perpendicular to said flat band section.

6. The brace as set forth in claim 1, wherein said first plurality of fixation rods is provided with two groups of at least three rods, each of said group attached to each of said ends of said upper frame member so that said groups are parallel to one anther, and wherein said second plurality of fixation rods is provided with two groups of at least three rods, each of said group attached to each of said ends of said lower frame member so that said groups are parallel to one another.

7. The brace as set forth in claim 6, wherein said fixation rods are of solid construction.

8. The brace as set forth in claim 1, wherein said second plurality of fixation rods are arcuately bent so as to follow the contour of the calf portion of said leg.

9. The brace as set forth in claim 1, wherein said plurality of fixation rods are tubular and have a circular cross-section.

10. The brace as set forth in claim 1, wherein said fixation rods are fabricated out of a material selected from the group consisting of aluminum, glass fiber reinforced plastic or carbon fiber.

11. The brace as set forth in claim 1, further comprising first and second padding blanks slidable onto the fixation rods of the upper half shell frame portion.

12. The brace as set forth in claim 11, wherein said padding blanks are releasably secured to said upper half shell frame portion.

13. The brace as set forth in claim 11, further comprising first and second padding blanks slidable onto the fixation rods of the lower half shell frame portion.

14. The brace as set forth in claim 13, wherein said padding blanks are releasably secured to said lower half shell frame portion.

15. The brace as set forth in claim 11, wherein each of said fastening straps have first and second ends and wherein said fastening straps are provided with hook and loop fasteners at each of said first and second ends for securing said first end to said second end.

16. The brace as set forth in claim 1, further comprising a knee brace pad secured to said upper and lower frame members for providing support to the patella of the knee.

* * * * *